United States Patent [19]

Watanabe et al.

[11] 4,432,939
[45] Feb. 21, 1984

[54] AMMONIA GAS ANALYZER

[75] Inventors: Atsuo Watanabe; Teruo Kaneko; Takeo Tanaka; Yoshio Saito, all of Kanagawa, Japan

[73] Assignee: Fuji Electric Co., Ltd., Kanagawa, Japan

[21] Appl. No.: 250,790

[22] Filed: Apr. 3, 1981

[30] Foreign Application Priority Data

Apr. 14, 1980 [JP] Japan .................................. 55-48815
Apr. 14, 1980 [JP] Japan ............................. 55-50358[U]

[51] Int. Cl.³ ...................... G01N 31/10; G01N 21/00
[52] U.S. Cl. ........................................ 422/93; 422/91; 422/240; 436/113; 436/158; 436/159
[58] Field of Search ................. 422/93, 83, 91, 240; 23/232 R; 436/113

[56] References Cited

U.S. PATENT DOCUMENTS

| | | | |
|---|---|---|---|
| 3,718,429 | 2/1973 | Williamson, Jr. | 422/83 X |
| 3,853,474 | 12/1974 | Austin | 23/232 R X |
| 3,904,371 | 9/1975 | Neti et al. | 23/232 R |
| 3,997,297 | 12/1976 | Jenkins et al. | 422/93 |
| 4,113,434 | 4/1978 | Tanaka et al. | 422/93 |

Primary Examiner—Michael S. Marcus

Attorney, Agent, or Firm—Sughrue, Mion, Zinn, Macpeak and Seas

[57] ABSTRACT

An ammonia gas analyzer and a sulfuric acid converter utilized in the ammonia gas analyzer in which a sample gas is maintained at a relatively high temperature prior to entering the sulfuric acid converter to thereby prevent acidic sulfuric acid sulfates and/or ammonia sulfates from crystallizing and being deposited on the walls of the device. The ammonia gas analyzer includes gas sampling means, a gas measuring channel connected to the gas sampling means, a comparison gas channel connected parallel to the measuring gas channel with the measuring gas channel including an $NH_3/NO$ converter for converting $NH_3$ in a sample gas into NO and means for measuring a concentration of $NH_3$ on the basis of variations of an amount of NO in the measuring gas channel with respect to that in the comparison gas channel. A first sulfuric acid converter has an inlet connected to the sampling means and an outlet connected to an inlet portion of the comparison gas channel for converting sulfuric acid, sulfate and sulfur trioxide in the sample gas into sulfur dioxide. A second sulfuric acid converter has an inlet connected to the outlet of the $NH_3/NO$ converter and an outlet connected to an inlet of the measuring means.

3 Claims, 5 Drawing Figures

AMMONIA GAS ANALYZER

BACKGROUND OF THE INVENTION

The present invention relates to an ammonia gas analyzer in which a sample gas containing NH₃ is fed to a measuring channel where NH₃ is converted into NO by a NH₃/NO converter and to a comparison channel where the concentration of NH₃ in the sample gas is measured with reference to an increase in the amount of NO₂ in the measuring channel. For example, combustion of fossil fuel results in large amounts of nitrogen oxides (NO$_x$) and/or sulfur trioxide (SO₃) which reacts with water to form sulfuric acid mist.

In order to exclude nitrogen oxides, for example, from the combustion exhaust gas, a nitrogen removal system utilizing a selective ammonia reduction method has been commonly used. In this nitrogen removing system, it is necessary to add an excess amount of ammonia to improve the efficiency of the nitrogen removing reaction of ammonia (NH₃) with nitrogen oxides. As a result of this, non-reacted ammonia is left at an outlet of the nitrogen removing apparatus and it is exhausted through a chimney.

Recently, the exhaust of ammonia has been recognized as a source of the pollution due mainly to its disagreeable odor and the ammonia content of industrial discharges has been subjected to regulation. Therefore, it is necessary to measure the concentration of ammonia in the exhaust gas continuously and accurately.

FIG. 1 shows schematically a conventional ammonia gas analyzer for measuring ammonia concentration using an infrared NO gas analyzer. In FIG. 1, a gas sampler 10 is inserted in a chimney through which a combination of exhaust gases flows. The gas sampler 10 includes a filter 11, a gas sampling tube 12 connected to the filter 11, a protective sheath 13 for protecting the filter and the sampling tube and a flange 14 for mounting the gas sampler 10 on a chimney wall.

Combustion exhaust gas (referred to as "sample gas" hereinafter) collected by the gas sampler 10 is fed to a measuring gas channel 20 and to a comparison gas channel 30 branching at the inlet of the channel 20. In the measuring gas channel 20, a NH₃/NO converter 21 for converting NH₃ contained in the sample gas into nitrogen monoxide (NO), a NO₂/NO converter 22 for converting nitrogen dioxide (NO₂) converted eventually from a portion of the NH₃ by the NH₃/NO converter 21 and contained in a gas therefrom into nitrogen monoxide (NO), a pump 23, a desiccator 24 and a filter 25 are disposed. A pump 33, a desiccator 34 and filter 35 are disposed in comparison channel 30. A NO₂/NO converter similar to the converter 22 should be included also in the comparison channel 30 if the exhaust gas itself contains NO₂. If there is no NO₂ in the exhaust gas and the NH₃/NO converter can convert it into NO completely, there is no need of providing the NO₂/NO converter 22 in the measuring gas channel 20.

The sample gas in the measuring gas system 20 is conducted to a measuring tank 43 of an infrared NO gas analyzer 40. The sample gas introduced to the comparison channel 30 is introduced into a comparison tank 44 provided in the channel 30. The infrared NO gas analyzer 40 includes a light source 41, a chopper 47 which is rotated by a motor 46 for chopping light from the light source 41, an optical separator 42 for separating the light from the light source into two light beams, the measuring tank 43, the comparison tank 44 and a detector 45 in which is filled NO gas. The measuring tank 43 and the comparison tank 44 are illuminated with light beams of equal intensity from the light source 41. These beams are adsorbed according to the amounts of NO in the channels 20 and 30.

Therefore, by detecting, with the detector 45, the difference in light intensity between the two light beams incident on the detector 45, it is possible to measure the difference of amounts of NO in the channels 20 and 30 to thereby determine the NH₃ gas concentration in the sample gas.

It is well known that combustion exhaust gas usually contains a SO₃ component which exists in the form of sulfur trioxide (SO₃), sulfuric acid mist (H₂SO₄) and/or sulfates such as ammonium sulfate [(NH₄)₂SO₄] and/or acidic ammonium sulfate [(NH₄)HSO₄]. Particularly, when the temperature is sufficiently low, sulfur trioxide and sulfuric acid mist react with ammonium according to the following formulas resulting in the production of sulfates.

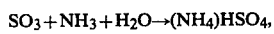

$$SO_3 + NH_3 + H_2O \rightarrow (NH_4)HSO_4,$$

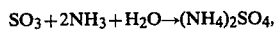

$$SO_3 + 2NH_3 + H_2O \rightarrow (NH_4)_2SO_4,$$

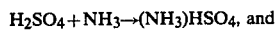

$$H_2SO_4 + NH_3 \rightarrow (NH_3)HSO_4, \text{ and}$$

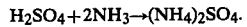

$$H_2SO_4 + 2NH_3 \rightarrow (NH_4)_2SO_4.$$

The sulfates usually crystallize at a temperature of 250° C. to 200° C. When the ammonia gas analyzer shown in FIG. 1 is used to analyze an exhaust gas containing an SO₃ component, the various tubular members constituting the measuring gas channel 20 and the comparison gas channel 30 tend to be closed by accumulations of crystallized sulfates and various parts thereof tend to be easily corroded by sulfuric acid components causing the ammonia gas analyzer to become inoperative or shortening the useful life thereof.

In order to resolve this difficulty, it may be enough to maintain the temperature of the members constituting the gas channels 20 and 30 at or above 250° C. However, a system for maintaining the temperature at such high temperature is complicated and expensive.

SUMMARY OF THE INVENTION

An object of the present invention is to provide an ammonia gas analyzer free from the disadvantages caused by SO₃ components contained in an exhaust gas.

Another object is to provide a sulfuric acid converter capable of converting sulfuric compounds such as sulfuric acid mist, sulfates and sulfur trioxides into sulfur dioxide, which may be disposed of at a downstream side of an NH₃/NO converter in the measuring gas channel of the analyzer and at an inlet of the comparison gas channel.

Another object of the present invention is to provide an improved sulfuric acid converter in which the sample gas can be kept at a relatively high temperature before entering the sulfuric acid converter to thereby prevent acidic sulfuric acid sulfates and/or ammonia sulfates from being produced.

In accordance with these and other objects of the invention, there is provided an ammonia gas analyzer in which a connecting portion between the branching point of the comparison gas channel and the sulfuric acid converter is constituted by a connecting tube for connecting the measuring channel and the sulfuric acid converter and an insertion tube coaxially arranged within the connecting tube for guiding the sample gas to the sulfuric acid converter. Also, the connecting portion between the outlet of the NH₃/NO converter and the sulfuric acid converter is constituted by a connecting tube connecting the NH₃/NO converter and the sulfuric acid converter and an insertion tube coaxially arranged with the connecting tube gas guiding the sample gas to the sulfuric acid converter.

DESCRIPTION OF THE PREFERRED EMBODIMENTS

Figure 1:
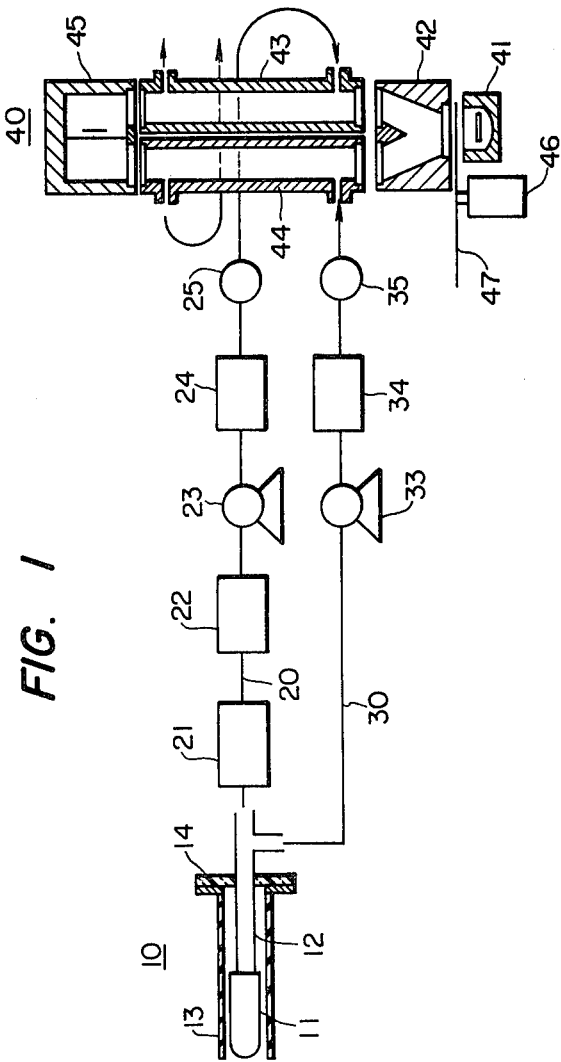
FIG. 1 is a schematic illustration of a conventional ammonia gas analyzer.
Figure 2:
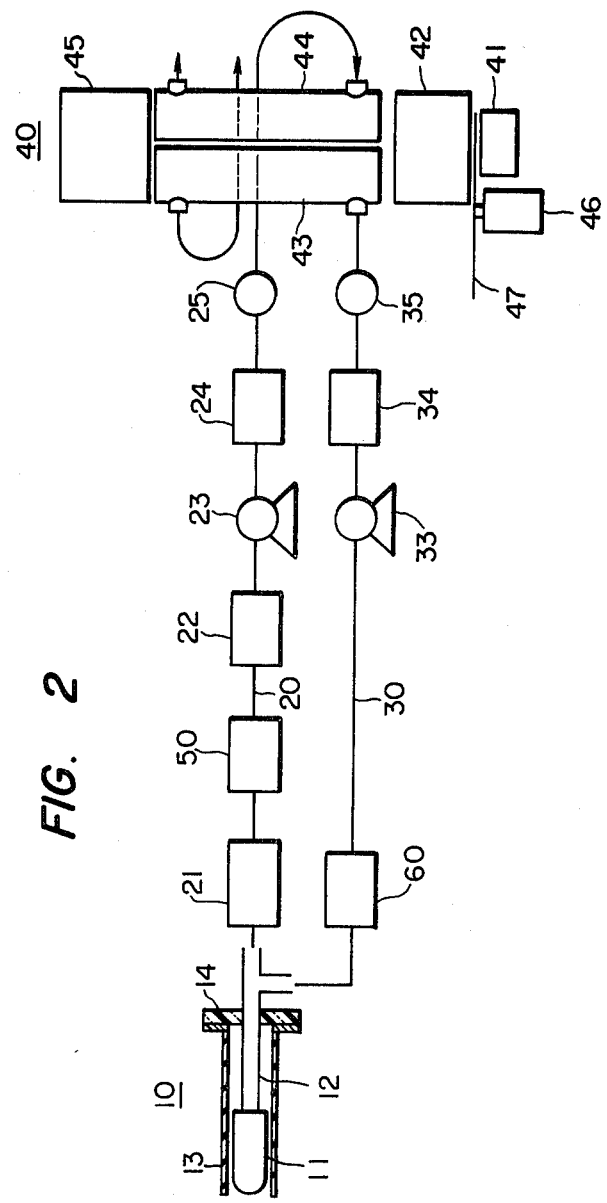
FIG. 2 is a schematic illustration of a preferred embodiment of an ammonia gas analyzer of the present invention.

In FIG. 2 shows a preferred embodiment of an ammonia gas analyzer of the present invention schematically in which similar components to those shown in FIG. 1 are indicated by the same reference numerals as those used in FIG. 1. The ammonia gas analyzer of FIG. 2 is different from that shown in FIG. 1 in that a sulfuric acid converter 50 is disposed in just the downstream side of the gas outlet of the NH₃/NO converter 21 of the measuring gas channel 20 and a similar sulfuric acid converter 60 is disposed in just the downstream side of the branching point of the comparison gas channel.

Figure 4:
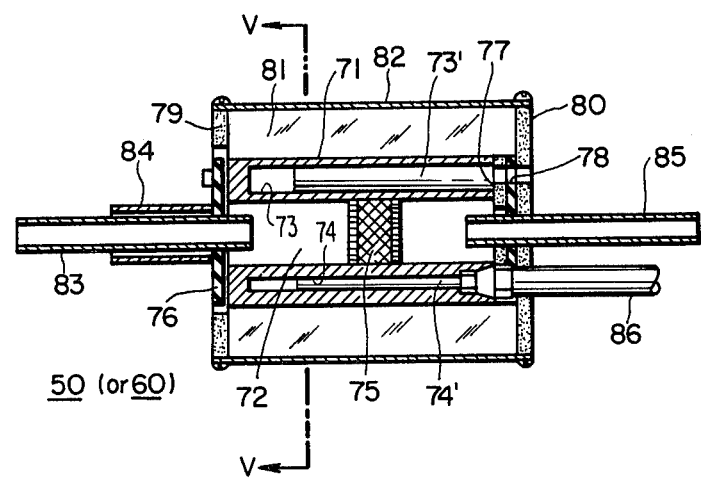
FIG. 4 is a cross-sectional view of a sulfuric acid converter according to the present invention.
Figure 5:
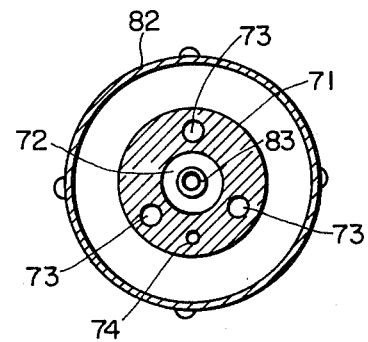
FIG. 5 is a cross section taken along a line V—V in FIG. 4.

Each of the sulfuric acid converters 50 and 60 is constructed as shown in FIG. 4. That is, a reaction chamber 71 is formed by providing a throughhole 72 in a block of anticorrosive material such as titanium. A plurality, three in this embodiment, of parallel blind holes 73 are also formed in a wall portion of the block 71. The blind holes 73 extend parallel to the throughhole 72 which serves as the reaction chamber. The blind holes 73 are positioned equiangularly. A blind hole 74 is also formed in the wall portion of the block 71 extending parallel to the blind holes 73, and is positioned between a pair of selected ones of the blind holes 73 as shown in FIG. 5. A cartridge heater 73' is inserted into each of the blind holes 73 to directly heat the block material to a temperature of about 400° C.

A temperature measuring element 74' is inserted into the blind hole 74 to signal the temperature of the reaction chamber 72 through a lead wire 86 to a temperature controlling device (not shown).

In the reaction chamber 72 in the block 71, a catalyst layer 75 of carbon material is disposed. A left side opening of the reaction chamber 72 is closed with a packing element by an inlet flange 76 which is bolted suitably to the wall portion of the block 71. The flange 76 is formed with a central throughhole through which an insertion tube 83 protrudes slightly into the reaction chamber 72. The insertion tube 83 is welded to the flange 76 in that position. A connecting tube 84, which is arranged coaxially with the insertion tube 83 encircling the latter, is welded to the flange 76.

A right-side opening of the reaction chamber 72 is closed through a heat resistant material sheet 77 such as asbestos by an outlet flange 78 which is fixedly secured to the latter by bolts. The outlet flange is formed with a central throughhole to which a conduit pipe 85 is welded so that it protrudes slightly into the reaction chamber 72 as in the case of the inlet flange 76. The outlet flange 78 is further formed with a plurality of throughholes in positions corresponding to the blind holes 73 and 74, respectively.

To the inlet and outlet flanges 76 and 78, side walls 79 and 80, respectively, of asbestos are secured. The diameters of the side walls 79 and 80 are the same and are larger than the outer diameter of the block 71. A cylindrical cover 82 together with the outer surfaces of the block 71 and the side walls 79 and 80 and the inlet and outlet flanges 76 and 78 define an annular space surrounding the block 71 which is filled with a thermal insulating material 81.

Figure 3:
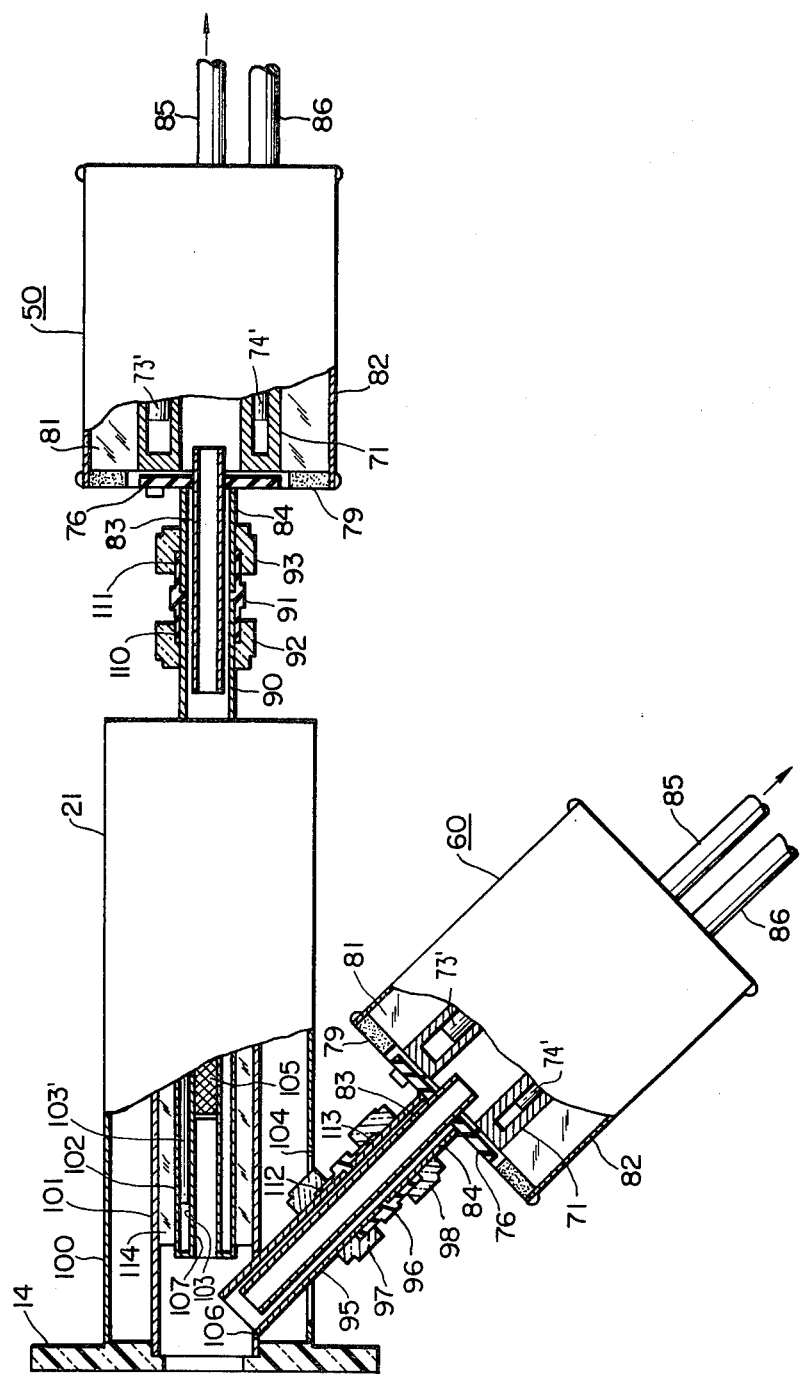
FIG. 3 is a detailed illustration of a primary portion of the analyzer of FIG. 2.

The sulfuric acid converter 50 is disposed at the gas outlet of the NH₃/NO converter in the measuring gas channel and the sulfuric acid converter 60, having the same structure, is disposed at the branching point in the comparison channel as shown in FIG. 3.

In FIG. 3, the NH₃/NO converter 21 in the measuring gas channel 20 has a reaction chamber block 102 which is formed with a central throughhole 107 serving as a reaction chamber and which also is provided with blind holes 103 into which cartridge heaters 103' are inserted. In the reaction chamber 107, a platinum catalyst layer 105 is disposed to convert NH₃ to NO. The layer 105 is heated up to about 600° C. to 900° C. by the cartridge heaters 103'. The reaction chamber block 102 is surrounded by a thermal insulating material 114 which fills an annular space defined by an inner surface of a conduit 101 and the outer surface of the block 102. The conduit 101 is coaxially disposed in a cylindrical cover member 100.

The conduit 101 is formed with an opening 106 on a wall thereof. The position of the opening 106 is just upstream of the reaction chamber 102 of the NH₃/NO converter 21 and one end of a connecting tube 95 is welded to the opening 106. The other end of the connecting tube 95 is inserted into one end of a sleeve 96 to which a cap nut 97 is screwed. A packing ring 112 having a wedge-shaped cross section is disposed on the inside of the cap nut 97 so that a tight connection between the sleeve 96 and the connecting tube 95 is obtained by tightening the cap nut 97. The connecting tube 84 of the sulfuric acid converter 60 is inserted into the sleeve 96 from the other end thereof.

A tight connection between the sleeve 96 and the connecting tube 84 of the sulfuric acid converter 60 is also obtained by tightening a cap nut 98 having a wedge packing ring 113. In this manner, the sulfuric acid converter 60 of the comparison channel 30 is connected to the hole 106 of the conduit 101. That is, the connection between the branching point of the comparison channel 30 and the sulfuric acid converter 60 is made up by a coaxial double tube structure composed of the connecting tubes 95 and 84 and the insertion tube 83.

On the other hand, one end of a connecting tube 90 is connected to the gas outlet of the NH₃/NO converter 21 and the other end thereof is inserted into a sleeve 91. The connection between the other tube end and the sleeve is strengthened by means of a cap nut 92 having a wedge-shaped packing ring 110 housed therein.

A connecting tube 84 of the sulfuric acid converter 50 is inserted into the other end portion of the sleeve 91 and connected rigidly thereto by means of a cap nut 93 having a wedge-shaped packing ring 111. Thus, the connection between the sulfuric acid converter 80 and the NH$_3$/NO converter 21 is made by a coaxial double tube structure including the connecting tubes 90 and 84 and the insertion tube 83.

NH$_3$ is converted by the NH$_3$/NO converter 21 in the measuring gas channel into NO according to the following reaction formula:

$$NH_3 + 5/4O_2 \rightarrow NO + 3/2H_2O.$$

Sulfur oxide components (sulfuric acid mist, sulfate and sulfur trioxide) contained in the sample gas are converted by the sulfuric acid converters 50 and 60 into sulfur dioxide according to the following formulas:

$$H_2SO_4 + C \rightarrow SO_2 + CO_x,$$

$$(NH_4)HSO_4 + C \rightarrow SO_2 + NH_3 + CO_x + H_2O,$$

$$(NH_4)_2SO_4 + C \rightarrow SO_2 + 2NH_3 + CO_x + H_2O, \text{ and}$$

$$SO_3 + C \rightarrow SO_2 + CO_x,$$

where $x = 1$ or 2.

The decomposition and/or crystallization temperature of sulfur dioxide (SO$_2$) and ammonia (NH$_3$) produced by the sulfuric acid converters 50 and 60 is relatively low, generally about 59° C. Therefore, by maintaining the temperature of the measuring and comparison gas channels after the sulfuric acid converters 50 and 60 at, for example, about 70° C., it is possible to prevent SO$_2$ and NH$_3$ from reacting with each other and crystallizing. Therefore, with the provision of the sulfuric acid converters 50 and 60 in the two channels, there is no need of providing a temperature control system for maintaining the temperature beyond the range from about 200° C. to about 250° C. which is necessary to prevent the crystallization of sulfuric acid mist and/or sulfates because it is only necessary to prevent the crystallization of sulfur dioxide which occurs at about 50° C. Thus the temperature control system for the channels 20 and 30 is simple.

It should be noted that although the sulfuric acid converter shown in FIGS. 4 and 5 is described as being incorporated in an ammonia gas analyzer, it can be used independently of the ammonia gas analyzer.

What is claimed is:

1. An ammonia gas analyzer comprising gas sampling means, a measuring gas channel connected to said gas sampling means, a comparison gas channel connected to said gas sampling means parallel to said measuring gas channel, said measuring gas channel including an NH$_3$/NO converter for converting NH$_3$ contained in a sample gas into NO and measuring means connected to said channels for measuring the concentration of NH$_3$ in the gas sampled by said gas sampling means by comparing the amount of NO in said measuring gas channel after conversion of the NH$_3$ with respect to the amount of NO in said comparison gas channel, a first sulphuric acid converter located in said comparison gas channel intermediate said sampling means and said measuring means and a second sulphuric acid converter located in said measuring gas channel intermediate said NH$_3$/NO converter and said measuring means for converting sulfuric compounds in said sample gas into sulfur dioxide.

2. The ammonia gas analyzer as claimed in claim 1 further comprising a connection between said inlet of said first sulfuric acid converter and said sampling means comprising a first inner tube and a first outer tube coaxially arranged with respect to said first inner tube, said first inner tube having an inlet opening to an outlet of said sampling means and an outlet opening to said first sulfuric acid converter, said first outer tube having an inlet opening to said outlet of said sampling means and an outlet closed to define an annular space around said first inner tube for preventing the temperature of sample gas introduced from said first sulfuric acid converter from dropping substantially, and a connection between said inlet of said second sulfuric acid converter and said outlet of said NH$_3$/NO converter comprising a second inner tube and a second outer tube coaxially arranged with respect to said second inner tube, said second inner tube having an inlet opening to said outlet of said NO$_3$/NO converter and an outlet opening to said second sulfuric acid converter, said second outer tube having an inlet opening to said outlet of said NO$_3$/NO converter and an outlet closed to form an annular space around said second inner tube for preventing the temperature of sample gas introduced into said second sulfuric acid converter from dropping substantially.

3. The ammonia gas analyzer as claimed in claim 1 or 2 wherein each of said first and second sulfuric acid converters comprises a reaction chamber block formed of a corrosion-resistant metal material having a central throughhole therein forming a reaction chamber, a plurality of first blind holes disposed substantially equiangularly around said central throughhole and extending parallel to said central throughhole and a second blind hole extending parallel to said central throughhole; a plurality of cartridge heater elements of a number corresponding to the number of said first blind holes, each of said cartridge heater elements being disposed in a corresponding one of said first blind holes; a temperature measuring element disposed in said second blind hole; a catalyst layer disposed in said central throughhole forming said reaction chamber for connecting sulfuric acid, sulfate and sulfur trioxide into sulfur dioxide; first flange means having a central opening and being adapted to be connected to one end of said reaction chamber block to close the inlet side of said central throughhole; an inner tube extending from a periphery of said central opening; an outer tube extending coaxially with said inner tube from said first flange means; and second flange means having a central opening forming an outlet and a plurality of peripherally arranged openings corresponding to said first and second blind holes of said reaction chamber block for accepting therein lead wires of said elements.

* * * * *